(12) United States Patent
Tanzi et al.

(10) Patent No.: US 7,514,576 B2
(45) Date of Patent: Apr. 7, 2009

(54) PROCESS FOR THE SEPARATION OF ALKYL BRANCHED FATTY ACIDS FROM A FATTY ACID MIXTURE

(75) Inventors: Steven Tanzi, Naperville, IL (US);
Aloisius R. M. Soeterboek, Poortugaal (NL); Erik T Brug, Waddinxveen (NL); Johannes J Vreewijk, Rotterdam (NL)

(73) Assignees: Unichema Chemie B.V., Gouda (NL); ICI Americas, Inc., New Castle, DE (US)

( * ) Notice: Subject to any disclaimer, the term of this patent is extended or adjusted under 35 U.S.C. 154(b) by 9 days.

(21) Appl. No.: 10/573,351

(22) PCT Filed: Sep. 20, 2004

(86) PCT No.: PCT/EP2004/010634
§ 371 (c)(1),
(2), (4) Date: Jan. 16, 2007

(87) PCT Pub. No.: WO2005/030693
PCT Pub. Date: Apr. 7, 2005

(65) Prior Publication Data
US 2007/0276148 A1    Nov. 29, 2007

(30) Foreign Application Priority Data
Sep. 25, 2003    (EP) .................................. 03256026

(51) Int. Cl.
*C11B 7/00*    (2006.01)

(52) U.S. Cl. ...................................................... 554/211
(58) Field of Classification Search ................. 554/208, 554/211
See application file for complete search history.

(56) References Cited

U.S. PATENT DOCUMENTS 5,917,097 A * 6/1999 Koehler et al. .............. 568/884

FOREIGN PATENT DOCUMENTS

| EP | 0145697 A2 * | 3/1991 |
| EP | 0415697 | 3/1991 |
| EP | 0492507 | 7/1992 |
| WO | 96/02619 | 2/1996 |
| WO | 99/20722 | 4/1999 |

OTHER PUBLICATIONS

Perkins, et al., Analyses of Fats and Oils and Derivatives, 1993, AOCS, pp. 14, 15.*

* cited by examiner

*Primary Examiner*—Daniel M Sullivan
*Assistant Examiner*—Yate' K Cutliff
(74) *Attorney, Agent, or Firm*—Jones Day

(57) ABSTRACT

A process for the separation of alkyl branched $C_{12}$ to $C_{24}$ fatty acids from a fatty acid mixture comprising linear and alkyl branched $C_{12}$ to $C_{24}$ fatty acids comprises; (i) optionally hydrogenating the fatty acid mixture, (ii) cooling the mixture to form crystals, and (iii) separating the alkyl branched $C_{12}$ to $C_{24}$ fatty acids from the mixture by dry fractionation.

24 Claims, No Drawings

PROCESS FOR THE SEPARATION OF ALKYL BRANCHED FATTY ACIDS FROM A FATTY ACID MIXTURE

CROSS REFERENCE TO RELATED APPLICATION

This application is the National Phase application of International Application No. PCT/EP2004/010634, filed Sep. 20, 2004, which designates the United States and was published in English. This application, in its entirety, is incorporated herein by reference.

FIELD OF INVENTION

The present invention relates to a process for the separation of alkyl branched fatty acids from linear fatty acids, and in particular to the separation of saturated alkyl branched fatty acids.

BACKGROUND

Alkyl branched fatty acids occur as a by-product of the catalytic or thermal dimerisation of unsaturated straight chain fatty acids. Such alkyl branched fatty acids are known as "isostearic acid". Isostearic acid is liquid at ambient temperature, exhibits better stability to oxidation than oleic acid, and consequently is a very useful product which is sold Into a wide range of application areas such as lubricant esters, and cosmetic applications. Isostearic acid is also used to make isostearyl alcohol. Isostearic acid is produced commercially by the so-called Emersol process.

In the Emersol process the fatty acid mixture is dissolved in organic solvent and then cooled down using horizontal scraped crystallisers. The linear fatty acid crystals which are formed during cooling are removed from the unsaturated linear fatty acids, unsaturated branched fatty acids and saturated branched fatty acids with a rotary drum filter. The solvent is then removed from both the fractions in a distillation step. The Emersol process is energy intensive, has high operational costs, and requires the use of undesirable organic solvent.

U.S. Pat. No. 4,973,431 A describes a wet separation process for the production of isostearic acid. In the wet separation process, the fatty acid mixture is also cooled down using horizontal scraped crystallisers. But then, a wetting agent solution, which is a mixture of water and surfactant, is added to the fatty acids. The linear fatty acid crystals are suspended in the aqueous phase and then separated from the mixture with a cold centrifuge. The linear fatty acids are then heated, breaking up the suspension and separated from the surfactant in a hot centrifuge. The use of both types of centrifuges results in high maintenance costs. The use of surfactant further increases the cost of the wet separation process.

A third technology, known as dry fractionation has been used to separate saturated fatty acids from unsaturated fatty acids, but it has not been applied to the separation of branched fatty acids. Dry fractionation involves the cooling of a fatty acid mixture in a crystalliser followed by squeezing the unsaturated fatty acid out of the solidified saturated fatty acid cake with a membrane filter

SUMMARY OF THE INVENTION

We have now discovered a process for the separation of alkyl branched fatty acids which reduces or substantially overcomes at least one of the aforementioned problems.

Accordingly, the present invention provides a process for the separation of alkyl branched $C_{12}$ to $C_{24}$ fatty acids from a fatty acid mixture comprising linear and alkyl branched $C_{12}$ to $C_{24}$ fatty acids which comprises;
 (i) optionally hydrogenating the fatty acid mixture,
 (ii) cooling the mixture to form crystals, and
 (iii) separating the alkyl branched $C_{12}$ to $C_{24}$ fatty acids from the mixture by dry fractionation.

The invention also provides an alkyl branched $C_{12}$ to $C_{24}$ fatty acid mixture comprising
 (i) less than 3% by weight of branched $C_{14}$ fatty acids,
 (ii) In the range from 2 to 12% by weight of branched $C_{16}$ fatty acids,
 (iii) in the range from 55 to 85% by weight of branched $C_{18}$ fatty acids,
 (iv) in the range from 2 to 12% by weight of branched $C_{20}$ fatty acids,
 (v) in the range from 1 to 8% by weight of branched $C_{22}$ fatty acids, and
 (vi) the weight ratio of $C_{18}$ to $C_{16}$ saturated linear fatty acids is in the range from 0.15 to 0.5:1.

The raw materials for the fatty acids used in the present invention are preferably naturally occurring materials such as triglyceride oils and can be of animal (e.g. tallow) or preferably of vegetable origin. Suitable fatty acids include sunflower fatty acids, soybean fatty acids, olive fatty acids, rapeseed fatty acids, linseed fatty acids, cottonseed fatty acids, safflower fatty acids, tall oil fatty acids and tallow olein. Relatively pure unsaturated fatty acids such as oleic acid, linoleic acid, linolenic acid, palmitoleic acid, and elaidic acid may be isolated, or relatively crude unsaturated fatty acid mixtures employed. Suitable unsaturated fatty acids are commercially available. These unsaturated fatty acids are subjected to a catalytic or thermal dimeristion process. One of the side products of the dimerisation process is known as the monomer fraction which is a complex fatty acid mixture of unsaturated alkyl branched fatty acids, saturated alkyl branched fatty acids, saturated linear fatty acids, and unsaturated linear fatty acids. This is the starting material for the process of the present invention.

The fatty add mixture starting material preferably comprises greater than 20%, more preferably in the range from 30 to 55%, particularly 35 to 50%, and especially 40 to 45% by weight of saturated fatty acids; and greater than 30%, more preferably in the range from 45 to 70%, particularly 50 to 65%, and especially 55 to 60% by weight of unsaturated fatty acids, both based on the total weight of fatty acids present.

The fatty acid mixture may be, and preferably is, hydrogenated using techniques known in the art, for example by using a nickel catalyst, in order to reduce the amount of unsaturated fatty adds. The hydrogenated fatty add mixture preferably comprises greater than 90%, more preferably greater than 93%, particularly greater than 95%, and especially greater than 97% by weight of saturated fatty acids; and in the range from 0 to 10%, more preferably less than 7%, particularly less than 5%, and especially less than 3% by weight of unsaturated fatty acids, both based on the total weight of fatty acids present.

The fatty acid mixture suitably comprises
 (i) in the range from 35 to 85%, preferably 40 to 65%, more preferably 45 to 60%, particularly 50 to 57%, and especially 51 to 55% by weight of alkyl branched $C_{12}$-$C_{24}$ fatty acids; and
 (ii) in the range from 15 to 65%, preferably 35 to 60%, more preferably 40 to 55%, particularly 43 to 50%, and especially 45 to 49% by weight of linear $C_{12}$-$C_{24}$ fatty acids, both based on the total weight of fatty acids present.

The alkyl branched and linear fatty acid mixture preferably comprises $C_{14}$ to $C_{22}$, more preferably $C_{16}$ to $C_{22}$, particularly $C_{18}$ to $C_{20}$, and especially $C_{18}$ fatty acids. The fatty acid mixture (i) preferably comprises in the range from 0 to 5%, more preferably less than 4%, particularly less than 3%, and especially less than 2% by weight of $C_{14}$ fatty acids, and/or
(ii) preferably comprises in the range from 5 to 50%, more preferably 10 to 35%, particularly 15 to 30%, and especially 20 to 25% by weight $C_{16}$ fatty acids, and/or
(iii) preferably comprises greater than 45%, more preferably in the range from 50 to 75%, particularly 55 to 65%, and especially 57 to 63% by weight of $C_{18}$ fatty acids, and/or
(iv) preferably comprises in the range from 0 to 20%, more preferably 3 to 15%, particularly 6 to 10%, and especially 7 to 9% by weight $C_{20}$ fatty acids, and or
(v) preferably comprises in the range from 0 to 12%, more preferably 2 to 10%, particularly 4 to 8%, and especially 5 to 7% by weight of $C_{22}$ fatty acids, all based on the total weight of fatty acids present.

In a particularly preferred embodiment of the present invention, the weight ratio of $C_{18}$ to $C_{18}$ saturated linear fatty acids present in the fatty acid mixture is suitably in the range from 0.3 to 2:1, preferably 0.4 to 1.5:1, more preferably 0.5 to 1.2:1, particularly 0.6 to 1.0:1, and especially 0.7 to 0.9:1. The aforementioned ratio may be, and preferably is, adjusted by the addition of saturated linear $C_{16}$ fatty acid, i.e. palmitic acid, to the fatty acid mixture prior to carrying out the process according to the present invention. The amount of palmitic acid added is preferably in the range from 0.5 to 15, more preferably 1 to 10, particularly 3 to 7, and especially 4 to 6 g per 100 g of fatty acid mixture starting material.

In the process according to the present invention the fatty acid mixture starting material is suitably initially heated so that it is in liquid state, preferably to a temperature above 45° C., more preferably in the range from 48 to 80° C., particularly 50 to 70° C., and especially 52 to 60° C. The fatty acid mixture starting material is preferably heated to a temperature in the range from 2 to 20° C., more preferably 5 to 15° C., particularly 7 to 13° C., and especially 9 to 11° C. above the titre (or melting point) of the mixture. The fatty acid mixture may be used directly from a distillation column, in which case the temperature, for example, can be as high as 110° C., which will require cooling to the aforementioned preferred temperature ranges prior to entering the crystallisers.

Crystallisation of the liquid fatty acid mixture is preferably achieved by cooling the fatty acid mixture below 18° C., more preferably below 17° C., particularly in the range from 7 to 16° C., and especially 5 to 15° C. The rate of cooling can have an important effect on the efficiency of the process, and in one embodiment of the invention cooling takes place in a batch-wise manner, preferably at a rate in the range from 1 to 30° C., more preferably 2 to 15° C., particularly 3 to 8° C., and especially 4 to 6° C. per hour. The batch-wise cooling process preferably takes place over a time period in the range from 1 to 14, more preferably 2 to 12, particularly 6 to 11, and especially 8 to 10 hours.

Alternatively and preferably, a continuous cooling process is employed, suitably cooling at a rate in the range from 15 to 140° C., preferably 25 to 100° C., more preferably 30 to 70° C., particularly 35 to 60° C. and especially 40 to 55° C. per hour. The continuous cooling process preferably takes place over a time period in the range from 0.1 to 4, more preferably 0.3 to 3, particularly 0.5 to 2, and especially 0.8 to 1.2 hours.

During the cooling process, crystallization of the saturated linear fatty acids occurs. In a particularly preferred embodiment of the present invention the composition of the fatty acid mixture after the cooling stage comprises in the range from 15 to 55% more preferably 20 to 50%, particularly 25 to 45%, and especially 30 to 40% by weight of liquid fatty acids; and in the range from 45 to 85% more preferably 50 to 80%, particularly 55 to 75%, and especially 60 to 70% by weight of solid fatty acids. In a further preferred embodiment, the solid fatty acids have a crystal shape that is plate-like in character, as opposed to the more normal needle-like structure. The plate-like crystals are approximately circular in shape, having a suitable mean aspect ratio $d_1:d_2$ (measured as described herein) (where $d_1$ and $d_2$, respectively, are the length and width of the crystal in the range from 1 to 3:1, preferably 1 to 2:1, more preferably 1 to 1.3:1, particularly 1 to 1.2:1, and especially 1 to 1.1:1. In a preferred embodiment of the invention, suitably at least 40%, preferably at least 55%, more preferably at least 70%, particularly at least 80%, and especially at least 90% by number of the crystals have an aspect ratio within the above preferred ranges given for the mean aspect ratio. The mean depth (or $d_3$) of the plate-like crystals is preferably less than 1/3, more preferably less than 1/4, particularly in the range from 1/50 to 1/8, and especially 1/20 to 1/10 of the mean crystal diameter (half the sum of the mean length and mean width $((d_1+d_2)/2)$).

The plate-like crystals suitably have a mean crystal diameter (measured as described herein) in the range from 150 to 600 μm, preferably 250 to 500 μm, more preferably 300 to 460 μm, particularly 350 to 440 μm, and especially 380 to 420 μm. In a preferred embodiment of the invention, suitably at least 40%, preferably at least 55%, more preferably at least 70%, particularly at least 80%, and especially at least 90% by number of the crystals have a crystal diameter within the above preferred ranges given for the mean crystal diameter.

The preferred plate-like crystal shape gives rise to an open arrangement of crystals in the filter cake which has a lower porosity than a filter cake made up of crystals that are needle-like in shape.

A filter cake formed from plate-like crystals requires less hydraulic pressure to achieve the same yield of liquid/solid fatty acid separation, and surprisingly leads to significantly purer products.

After cooling, the fatty acid mixture is filtered, preferably through a suitable filter. The filter cloth is preferably made of polyolefin, more preferably polypropylene, fibers in particular, in the form of a weave. The fibers may be coated, preferably with a hydrophobic material such as PTFE. The weight of the filter cloth is preferably in the range from 200 to 600, more preferably 300 to 500, and particularly 350 to 450 g.m$^{-2}$. The filter cloth preferably has a permeability in the range from 0.1 to 10, more preferably 0.5 to 5, and particularly 1 to 2 I.dm$^{-2}$.min$^{-1}$. Suitable filter cloths are commercially available. The filter cloths are generally housed in filter presses which are also commercially available.

The filtration stage preferably takes place under pressure, more preferably in the range from 5 to 40, particularly 15 to 35, and especially 25 to 30 bar.

The alkyl branched $C_{12}$ to $C_{24}$ fatty acid mixture produced according to the process of the present invention preferably comprises greater than 70%, more preferably in the range from 73 to 95%, particularly 77 to 90%, and especially 80 to 85% by weight of branched fatty acids, and less than 30%, more preferably in the range from 5 to 27%, particularly 10 to 23%, and especially 15 to 20% by weight of linear fatty acids, both based on the total weight of fatty acids present.

The alkyl branched $C_{12}$ to $C_{24}$ fatty acid mixture preferably comprise $C_{14}$ to $C_{22}$, more preferably $C_{16}$ to $C_{22}$ fatty acids, particularly $C_{18}$ to $C_{20}$, and especially $C_{18}$ fatty acids. The alkyl branched fatty acid mixture preferably comprises (i) in the range from 0 to 4%, more preferably less than 3%, particularly less than 2%, and especially less than 1% by weight of branched $C_{14}$ fatty acids, and/or
(ii) in the range from 0 to 15%, more preferably 2 to 12%, particularly 4 to 10%, and especially 6 to 8% by weight of branched $C_{16}$ fatty acids, and/or
(iii) greater than 50%, more preferably in the range from 55 to 85%, particularly 60 to 80%, and especially 65 to 75% by weight of branched $C_{18}$ fatty acids, and/or (iv) in the range from 0 to 15%, more preferably 2 to 12%, particularly 4 to 10%, and especially 6 to 8% by weight of branched $C_{20}$ fatty acids, and or (v) preferably comprises in the range from 0 to 12%, more preferably 1 to 8%, particularly 1.5 to 6%, and especially 2 to 4% by weight of branched $C_{22}$ fatty acids, all based on the total weight of fatty acids present.

In addition, the alkyl branched fatty acid mixture preferably comprises (i) in the range from 0 to 18%, more preferably 3 to 12%, particularly 5 to 10%, and especially 6 to 8% by weight of linear $C_{16}$ fatty acids, and/or (ii) in the range from 0 to 10%, more preferably in the range from 0.5 to 6%, particularly 1 to 4% and especially 1.5 to 3% by weight of linear $C_{18}$ fatty acids, both based on the total weight of fatty acids present.

The weight ratio of $C_{18}$ to $C_{16}$ saturated linear fatty acids present in the branched fatty acid mixture is suitably in the range from 0.05 to 1:1, preferably 0.1 to 0.7:1, more preferably 0.15 to 0.5:1, particularly 0.2 to 0.4:1, and especially 0.25 to 0.35:1.

The alkyl branched $C_{12}$ to $C_{24}$ fatty acid mixture preferably comprises greater than 90%, more preferably in the range from 92 to 99.9%, particularly 95 to 99.5%, and especially 96 to 99% by weight of saturated fatty acids; and in the range from 0 to 10%, more preferably 0.1 to 8%, particularly 0.5 to 5%, and especially 1 to 4% by weight of unsaturated fatty acids, both based on the total weight of fatty acids present.

The alkyl branched $C_{12}$ to $C_{24}$ fatty acids produced according to the present invention preferably comprise alkyl side branches (attached directly to a carbon atom of the longest linear chain) having on average less than 3, more preferably less than 2.5, particularly in the range from 1.05 to 2, and especially 1.1 to 1.4 carbon atoms, i.e. the side branches are predominantly methyl groups. In a preferred embodiment of the invention, greater than 50%, more preferably greater than 60%, particularly in the range from 70 to 97%, and especially 80 to 93% by number of the side-branched groups are methyl groups. In a further preferred embodiment, greater than 30%, more preferably greater than 40%, particularly in the range from 45 to 90%, and especially 50 to 80% by number of the branched fatty acids contain single methyl side branches.

The alkyl branched $C_{12}$ to $C_{24}$ fatty acids preferably have an acid value (measured as described herein) in the range from 160 to 220, more preferably 175 to 205, particularly 182 to 196, and especially 187 to 191 mgKOHg$^{-1}$.

The alkyl branched $C_{12}$ to $C_{24}$ fatty acids preferably have a saponification value (measured as described herein) in the range from 165 to 220, more preferably 175 to 210, particularly 185 to 200, and especially 191 to 195 mgKOH.g$^{-1}$.

The alkyl branched $C_{12}$ to $C_{24}$ fatty acids preferably have an unsaponifiable content (measured as described herein) of less than 10, more preferably less than 7, particularly in the range from 0.5 to 5, and especially 1 to 3 g.100 g$^{-1}$.

The alkyl branched $C_{12}$ to $C_{24}$ fatty acids preferably have an iodine value (measured as described herein) of less than 8, more preferably less than 6, particularly in the range from 0.5 to 4, and especially 1 to 3 g iodine.100 g$^{-1}$.

The alkyl branched $C_{12}$ to $C_{24}$ fatty acids suitably have a cloud point (measured as described herein) in the range from 0 to 15° C., preferably 0 to 10° C., more preferably 0 to 8° C., particularly 0 to 6° C., and especially 0 to 4° C.

The alkyl branched $C_{12}$ to $C_{24}$ fatty acids suitably have a colour (measured as described herein) of less than 250, more preferably less than 150, particularly less than 100, and especially less than 50 Hazen units.

The invention is illustrated by the following non-limiting example. All parts and percentages are by weight unless otherwise indicated.

In this specification the following test methods have been used.

(i) Acid Value

The acid value was measured using the A.O.C.S. Official method Te 1a-64 (Reapproved 1997), and expressed as the number of milligrams of potassium hydroxide required to neutralise the free fatty acids in one gram of sample.

(ii) Saponification Value

The saponification value was determined using the A.O.C.S. Official Method TI 1a-64 (1997) and is defined as the number of milligrams of potassium hydroxide which reacts with one gram of sample under the prescribed conditions.

(iii) Unsaponifiable Value

The unsaponifiable value was measured using the A.O.C.S. Official Method, Ca6b-53 (1989).

(iv) Iodine Value

The iodine value was determined by the Wijs method (A.O.C.S. Official Method Tg 1-64 (1993)) and expressed as the number of grams of iodine absorbed by 100 grams of sample under the defined test conditions.

(v) Cloud Point

The cloud point was measured according to the A.O.C.S. Official Method (Cc 6-25).

(vi) Colour

Colour was determined using the Method of Colour Determination in Hazen Units (Pt—Co scale), ISO 2211 (1973).

(vii) Titre

Titre (or melting point) was measured according to A.O.C.S. Official Method, Tr1a-64 (1989).

(viii) Fatty Acid Composition

The fatty acid composition (chain length, saturated/unsaturated, linear/branched) was determined using gas chromatography, using the method ISO 5508:1990(E) Animal and vegetable fats and oils—Analysis by gas chromatography of methyl esters of fatty acids.

(ix) Crystal Size

Particle size of the plate-like crystals was measured by observing samples with an optical light microscope (Olympus BX60) under transmitted light combined with polarised light visualisation with magnification. Instead of a normal microscope stage, the samples were placed on a Linkham THMS 600 temperature programmable stage. A sample of fatty acid mixture was heated at a rate of 25° C.min$^{-1}$ until the crystals melted. After melting had occurred, heating was stopped and the sample was allowed to cool (no forced cooling was applied) until crystals were formed. Photographs were produced at an appropriate magnification, such that about 50 crystals were displayed in each photograph. A minimum number of 300 crystals were sized manually using a transparent size grid. The mean crystal diameter was calculated from the above measurements. In addition, the aspect ratio of the crystals was determined from the maximum (length) and minimum (width) dimensions of at least 50 particles. Alternatively, the measurements could be performed by computerised image analysis.

EXAMPLES

Example I 25 kg of a fatty acid mixture derived from the monomer fraction of a dimerisation process and at a temperature of 60° C. was charged to a vertical batch crystalliser of stainless steel construction, equipped with jacketted cooling and a vertically-mounted stirrer which could scrape the inner walls of the vessel. The fatty acid mixture was cooled under stirring during 7 hours to a temperature of 5° C. to form a slurry. The slurry was pumped to a membrane filter press equipped with polypropylene filter cloths. The whole filter press was cooled and maintained at a temperature of 5° C. Hydraulic pressure (via the filter press cooling fluid) was applied to the filter press and was increased at a rate of 1 bar.min$^{-1}$ to a pressure of 12 bar. The liquid phase (filtrate) exiting the filter press was collected. The pressure on the filter press was released and the solid phase (residue) was discharged and collected.

The resultant filtrate was analysed and found to have the following composition;
(i) 0.8% by weight of branched $C_{14}$ fatty acids,
(ii) 5.7% by weight of branched $C_{16}$ fatty acids,
(iii) 74.3% by weight of branched $C_{18}$ fatty acids,
(iv) 6.6% by weight of branched $C_{20}$ fatty acids,
(v) 1.9% by weight of branched $C_{22}$ fatty acids, and
(v) 5.2% by weight of linear $C_{16}$ fatty acids, and
(vi) 1.5% by weight of linear $C_{18}$ fatty acids.

The invention claimed is:

1. A process for the separation of alkyl branched $C_{12}$ to $C_{24}$ fatty acids from a fatty acid mixture comprising 15 to 65% by weight of linear $C_{12}$ to $C_{24}$ fatty acids and 35 to 85% by weight of alkyl branched $C_{12}$ to $C_{24}$ fatty acids, relative to the total weight of the fatty acid mixture, wherein the process comprises:
   (i) optionally hydrogenating the fatty acid mixture,
   (ii) cooling the mixture to form crystals, and
   (iii) separating the alkyl branched $C_{12}$ to $C_{24}$ fatty acids from the mixture by dry fractionation.

2. A process according to claim 1 wherein the fatty acid mixture comprises greater than 95% by weight of saturated fatty acids, and less than 5% by weight of unsaturated fatty acids.

3. A process according to claim 1 wherein the fatty acid mixture comprises 40 to 65% by weight of alkyl branched $C_{12}$ to $C_{24}$ fatty acids, and in the range from 35 to 60% by weight of linear $C_{12}$ to $C_{24}$ fatty acids.

4. A process according to claim 1 wherein the fatty acid mixture comprises
   (i) less than 4% by weight of $C_{14}$ fatty acids, and/or
   (ii) in the range from 10 to 35% by weight $C_{16}$ fatty acids, and/or
   (iii) in the range from 50 to 75% by weight of $C_{18}$ fatty acids, and/or
   (iv) in the range from 3 to 15% by weight of $C_{20}$ fatty acids, and/or
   (v) in the range from 2 to 10% by weight of $C_{22}$ fatty acids.

5. A process according to claim 1 wherein the fatty acid mixture comprises in the range from 15 to 30%, by weight $C_{16}$ fatty acids.

6. A process according to claim 1 wherein the fatty acid mixture comprises in the range from 55 to 65%, by weight of $C_{18}$ fatty acids.

7. A process according to claim 1 wherein the weight ratio of $C_{18}$ to $C_{16}$ saturated linear fatty acids present in the fatty acid mixture is in the range from 0.4 to 1.5:1.

8. A process according to claim 1 wherein the separated alkyl branched $C_{12}$ to $C_{24}$ fatty acids comprise in the range from 73 to 95% by weight of branched fatty acids, and in the range from 5 to 27% by weight of linear fatty acids.

9. A process according to claim 1 wherein the separated alkyl branched $C_{12}$ to $C_{24}$ fatty acids comprise
   (i) less than 3% by weight of branched $C_{14}$ fatty acids, and/or
   (ii) in the range from 2 to 12% by weight of branched $C_{16}$ fatty acids, and/or
   (iii) in the range from 55 to 85% by weight of branched $C_{18}$ fatty acids, and/or
   (iv) in the range from 2 to 12% by weight of branched $C_{20}$ acids, and/or
   (v) in the range from 1 to 8% by weight of branched $C_{22}$ fatty acids.

10. A process according to claim 1 wherein the separated alkyl branched $C_{12}$ to $C_{24}$ fatty acids comprise in the range from 4 to 10% by weight of branched $C_{16}$ fatty acids.

11. A process according to claim 1 wherein the separated alkyl branched $C_{12}$ to $C_{24}$ fatty acids comprise in the range from 60 to 80%, by weight of branched $C_{18}$ fatty acids.

12. A process according to claim 1 wherein the separated alkyl branched $C_{12}$ to $C_{24}$ fatty acids comprise
   (i) in the range from 3 to 14% by weight of linear $C_{16}$ fatty acids, and/or
   (ii) in the range from 0.5 to 6% by weight of linear $C_{18}$ fatty acids.

13. A process according to claim 1 wherein the separated alkyl branched $C_{12}$ to $C_{24}$ fatty acids comprise $C_{18}$ to $C_{16}$ saturated linear fatty acids present at a weight ratio in the range from 0.1 to 0.7:1.

14. A process according to claim 1 wherein the separated alkyl branched $C_{12}$-$C_{24}$ fatty acids comprise greater than 90% by weight of saturated fatty acids, and in the range from 0 to 10% by weight of unsaturated fatty acids.

15. A process according to claim 1 wherein the separated alkyl branched $C_{12}$-$C_{24}$ fatty acids have
   (i) an acid value in the range from 175 to 205 mgKOH.g$_{-1}$, and/or
   (ii) a saponification value in the range from 175 to 210 mgKOH.g$_{-1}$, and/or
   (iii) an unsaponifiable value of less than 7 g.100 g$_{-1}$, and/or
   (iv) an iodine value of less than 6 g.100 g$_{-1}$, and/or
   (v) a cloud point in the range from 0 to 10° C., and/or
   (vi) a colour value of less than 150 Hazen units.

16. A process according to claim 1 wherein the separated alkyl branched $C_{12}$ to $C_{24}$ fatty acids have a cloud point in the range from 0 to 80° C.

17. A process according to claim 1 wherein plate-like crystals are formed during cooling.

18. A process according to claim 17 wherein the plate-like crystals have a mean aspect ratio in the range from 1 to 2:1.

19. A process according to claim 17 wherein the plate-like crystals have a mean crystal diameter in the range from 250 to 500 μm.

20. A process according to claim 1 wherein the fatty acid mixture is initially heated to a temperature in the range from 48 to 80° C.

21. A process according to claim 1 wherein the fatty acid mixture is cooled to a temperature in the range from 7 to 16° C.

22. A process according to claim 1 wherein the alkyl branched $C_{12}$ to $C_{24}$ fatty acids are separated by filtration.

23. A process according to claim 1 wherein the weight ratio of $C_{18}$ to $C_{16}$ saturated linear fatty acids present in the fatty acid mixture is adjusted prior to or during the cooling stage, preferably by the addition of palmitic acid.

24. A process according to claim 23 wherein in the range from 0.5 to 15 g of palmitic acid is added per 100 g of fatty acid mixture.

* * * * *

UNITED STATES PATENT AND TRADEMARK OFFICE
CERTIFICATE OF CORRECTION

PATENT NO. : 7,514,576 B2
APPLICATION NO. : 10/573351
DATED : April 7, 2009
INVENTOR(S) : Steven Tanzi et al.

It is certified that error appears in the above-identified patent and that said Letters Patent is hereby corrected as shown below:

Title Page, Item (75)
The spelling of the name of the fourth listed inventor, Johannes J. Vreewijk, should be corrected to read as:

Johannes J. Vreeswijk

Signed and Sealed this

Thirtieth Day of June, 2009

JOHN DOLL
*Acting Director of the United States Patent and Trademark Office*